(12) United States Patent
Mayeaux

(10) Patent No.: US 8,468,899 B1
(45) Date of Patent: Jun. 25, 2013

(54) WET NATURAL GAS SAMPLING METHOD AND APPARATUS

(75) Inventor: Donald P. Mayeaux, Gonzales, LA (US)

(73) Assignee: A+ Manufacturing, LLC, Gonzales, LA (US)

( * ) Notice: Subject to any disclaimer, the term of this patent is extended or adjusted under 35 U.S.C. 154(b) by 673 days.

(21) Appl. No.: 12/618,696

(22) Filed: Nov. 13, 2009

Related U.S. Application Data

(60) Provisional application No. 61/115,067, filed on Nov. 15, 2008.

(51) Int. Cl.
*G01N 1/20* (2006.01)

(52) U.S. Cl.
USPC ............ 73/863.43; 73/863.51; 73/863.52; 73/863.58

(58) Field of Classification Search
USPC .................... 73/863.41, 863.43, 863.58
See application file for complete search history.

(56) References Cited

U.S. PATENT DOCUMENTS

| | | | | |
|---|---|---|---|---|
| 4,057,393 | A | * | 11/1977 | Budzak et al. ............. 436/141 |
| 4,426,880 | A | * | 1/1984 | Walters et al. ............ 73/61.62 |
| 2006/0286492 | A1 | * | 12/2006 | Morrisroe .................. 431/2 |
| 2007/0193373 | A1 | * | 8/2007 | Xie et al. ................ 73/863.03 |

FOREIGN PATENT DOCUMENTS

SU 892129 B * 12/1981

* cited by examiner

*Primary Examiner* — Hezron E Williams
*Assistant Examiner* — Paul West
(74) *Attorney, Agent, or Firm* — Joseph T Regard, Ltd plc

(57) ABSTRACT

A system for on-stream sampling of pressurized process gas such as natural gas or the like, said pressurized process gas having liquid entrained therein, or otherwise referenced as "wet". The preferred embodiment of the present invention contemplates a system for obtaining an accurate sample of said wet process gas, as well as providing an apparatus for obtaining same.

21 Claims, 12 Drawing Sheets

WET NATURAL GAS SAMPLING METHOD AND APPARATUS

DOMESTIC PRIORITY DATA AS CLAIMED BY APPLICANT

The present application claims the benefit of Provisional Application 61/115,067 filed Nov. 15, 2008 entitled "Wet Natural Gas Sampling Method and Apparatus".

TECHNICAL FIELD OF THE INVENTION

The present invention relates to sampling of pressurized process gas, and in particular to a system for on-stream sampling of pressurized process gas such as natural gas or the like, said pressurized process gas having liquid entrained therein, or otherwise referenced as "wet". The preferred embodiment of the present invention contemplates a system for obtaining an accurate sample of said wet process gas. Further provided is a system for breaking up entrained liquid in the stream into small liquid droplets, so that they are suspended in the flowing gas stream to form a sampling area for isokinetic sampling of the gas/liquid droplet stream.

BACKGROUND OF THE INVENTION

Natural gas is bought and sold based on its heating value. It is the BTU content that determines the monetary value of a given volume of natural gas. This BTU value is generally expressed in decatherms (one million BTU). In the determination of total heat value of a given volume of gas, a sample of the gas is analyzed and from the composition its heat value per unit volume is calculated. This value is generally expressed in BTU/cu ft. The typical range of transmission quality gas ranges between 1000 and 1100 BTU/cu ft. Production gas can have heating values exceeding 1500 BTU/cu ft.

There has been a long standing controversy between gas producers and gas transporters regarding entrained liquid typically present in most high BTU/cu ft gas (rich or wet gas). Transporter tariffs require essentially liquid-free gas. Hydrocarbon liquid in the gas being transported causes operational and safety problems. The practice is to separate the liquid before entering a transport (pipe) line.

The API 14.1 standards (Manual of Petroleum Measurement Standards, 2006) scope does not include "wet gas" "(a term referenced by the Natural Gas industry as a gas that is at its hydrocarbon dew point temperature and/or contains entrained liquid), nor does the GPA 2166 standard (Obtaining Natural Gas Samples for Analysis by Gas Chromatography, 2005). In summary, there is no known standard which defines how to obtain a "representative sample" of a natural gas supply having entrained hydrocarbon in any form.

The liquid hydrocarbon (HC) content of a Natural gas is comprised mainly of the heavier (higher molecular weights such as propane, ethane and octane) components. Therefore its heating value is high, and of great monetary value. This is the reason that producers wish to have the liquid HC represented in the sample composition utilized for computing the BTU/cu ft content.

The API 14.1 standard, Appendix B section B-3 Multiphase Flow states that:

"Sampling of multiphase flow is outside the scope of this standard. Sampling of multiphase (gas and liquid) mixtures is not recommended and should be avoided if at all possible. In the multiphase flow, the ideal system would mix the gas and liquid flows uniformly and collect a sample of the true mixture flowing in the line by using a properly designed sample probe and an isokinetic sampling system. Current technology of natural gas sampling is not sufficiently advanced to accomplish this with reasonable accuracy. When sampling a multiphase liquid-gas flow, the recommended procedure is to eliminate the liquid from the sample. The liquid product that flows through the line should be determined by another method. The liquid fraction of the multiphase flow may contain water and hydrocarbons. The hydrocarbons can contribute significantly to the energy (measured in British thermal units) content of the gas and their presence in the gas line must not be overlooked."

The GPA 2166 standard's scope states that the standard is not designed for sampling Natural gas that is at or below its HC dew point temperature. Within the body of this standard several references are made to avoiding liquid entrainment and condensation due to its impact on sample composition and the calculated heat value.

The API 14.1 and GPA 2166 are the primary standards utilized by most Gas companies to guide their sampling methods. Both state that they are not intended for obtaining a Natural gas sample representing a combined gas and liquid.

There have been many attempts to achieve the representative sampling of Natural gas/HC liquid mixture. Most methods use a dynamic flow isokinetic technique. In an ideal world, gas having liquid droplets suspended would be directed into the entrance port of a sample probe (isokinetic probe), without changing its velocity or direction of liquid droplets.

To accomplish this, the supply gas velocity must be known, 1) the gas velocity at the probe entrance must be maintained equal to the supply gas velocity, and 2) the probe entry design must be shaped such as not to disturb the flow pattern of the liquid droplets. This approach, even under closely controlled conditions, is not accurate enough for custody transfer measurement. Therefore, it is neither a good nor a practical method for sampling wet gas on an "ongoing" basis.

Additionally there are two other forms of liquid which may be present in the transport line other than suspended liquid droplets. One form is a liquid film which is always present when suspended droplets are flowing with the gas stream. Another form is liquid which at times flows along the bottom of the transport pipe. It is never known how the liquid is distributed between these three forms. Therefore measurement of only the suspended droplets is not on indication of the total liquid present in the transport line.

There is a company named Petrotech as of Kvala, Norway (hereinafter PETROTECH) which utilizes an isokinetic Natural gas technique called ISOSPLIT®. The method consists of static mixing the two phases followed by dynamic isokinetic sampling of the resulting mixture. As previously stated this technique is difficult to execute and produces less than desirable results. It is primarily employed at the well head. The PETROTECH U.S. Pat. No. 5,538,344 relates primarily to the positioning of a mixing body within a pipeline.

Another reason for requiring accuracy in the sampling of wet natural gas is that reservoir simulation models are based on compositional analysis, and gas allocations are also made on that basis.

With the dynamic isokinetic sampling technique, sample gas flows continuously during the sampling process.

In conclusion, the above isokinetic sampling systems are designed to insure an isokinetic fluid flow of process gas into the opening of a probe and therethrough to an external location. With such a configuration, the fluid stream velocity must be known and the fluid velocity entering the probe must be controlled, which makes the technique generally impractical for typical field sampling of fluids.

GENERAL SUMMARY DISCUSSION OF THE INVENTION

Unlike the above discussed, prior art dynamic isokinetic sampling systems, the present invention teaches a new and innovative "static isokinetic" sampling process, wherein a volume of the source fluid flowing through a conduit or pipeline is captured by a streamlined container arrangement suspended in said source fluid, providing a trapped fluid source with nominal flow disturbance, which trapped fluid is subsequently withdrawn and isolated in a location outside of the source fluid flowing stream, providing a static mode for isokinetically collecting and withdrawing the sample from the process fluid stream. Unlike the dynamic isokinetic techniques, the system of the present invention insures that the sample container will always be filled isokinetically even when pipeline velocities are rapidly changing.

Where the gas stream contains entrained liquid not in droplet form, there is provided a conditioning apparatus upstream the collection apparatus to break up entrained liquid in the gas stream into small droplets suspended by the gas stream, in order to provide a collection zone in the vicinity of the collection apparatus wherein there is provided the desired gas and liquid droplet mixture.

The present invention provides a far superior sampling solution for wet gas streams, including high HC dew point gases, which traditionally have been difficult to sample dynamically due to phase changes and resulting composition changes which can be triggered by flow, pressure, and/or temperature.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 3 is a side, partially cut-away view of the invention of FIG. 1, wherein the container having said sample gas therein is raised into the housing, and sealed via plugs or the like.

DETAILED DISCUSSION OF THE INVENTION

Figure 1:
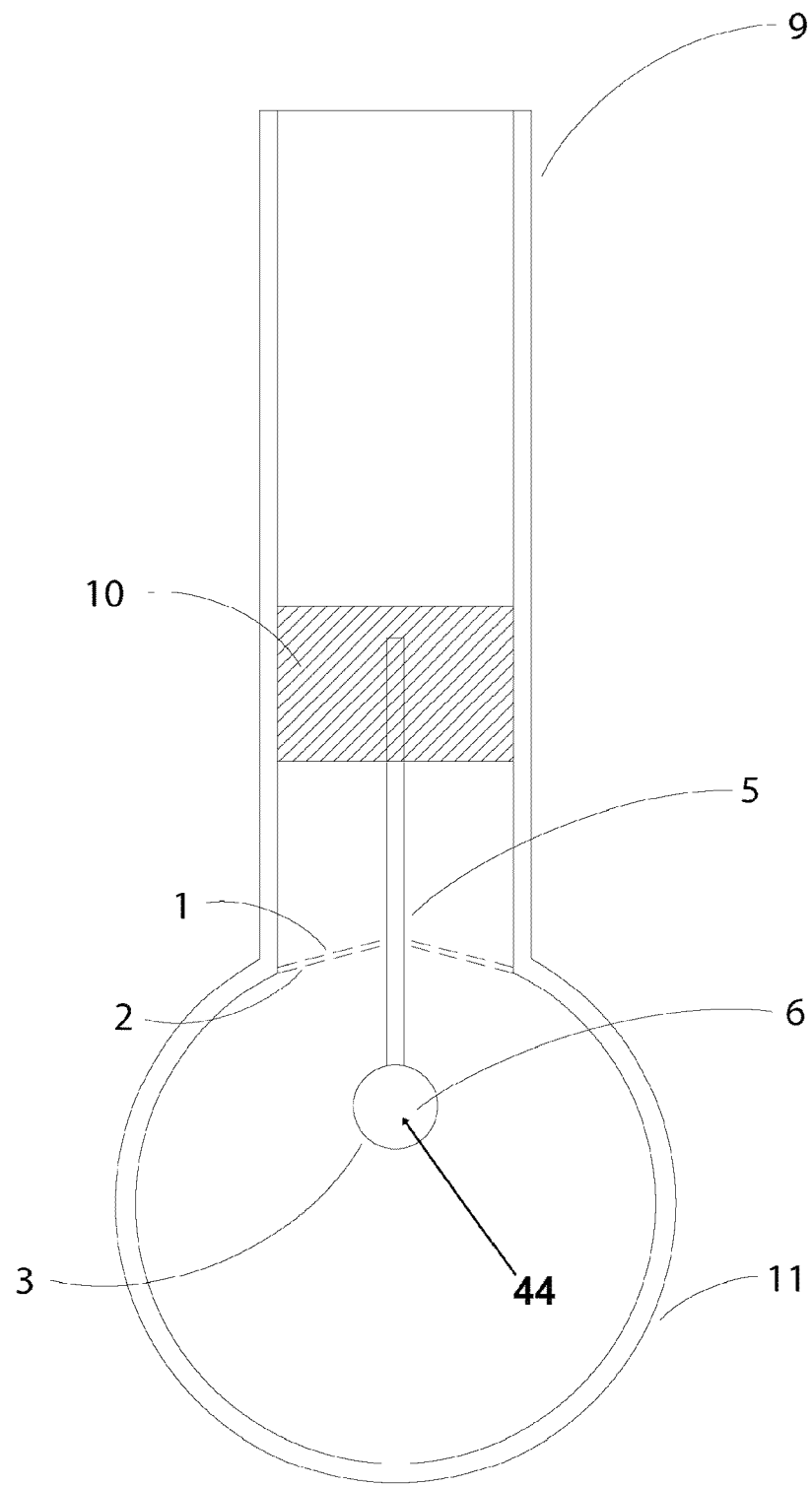
FIG. 1 is an end, partially cut-away view of the first embodiment of the sample collection system present invention, illustrating a cylindrical sample container which has been lowered from a housing into a pipeline containing a process gas stream containing entrained liquid.
Figure 2:
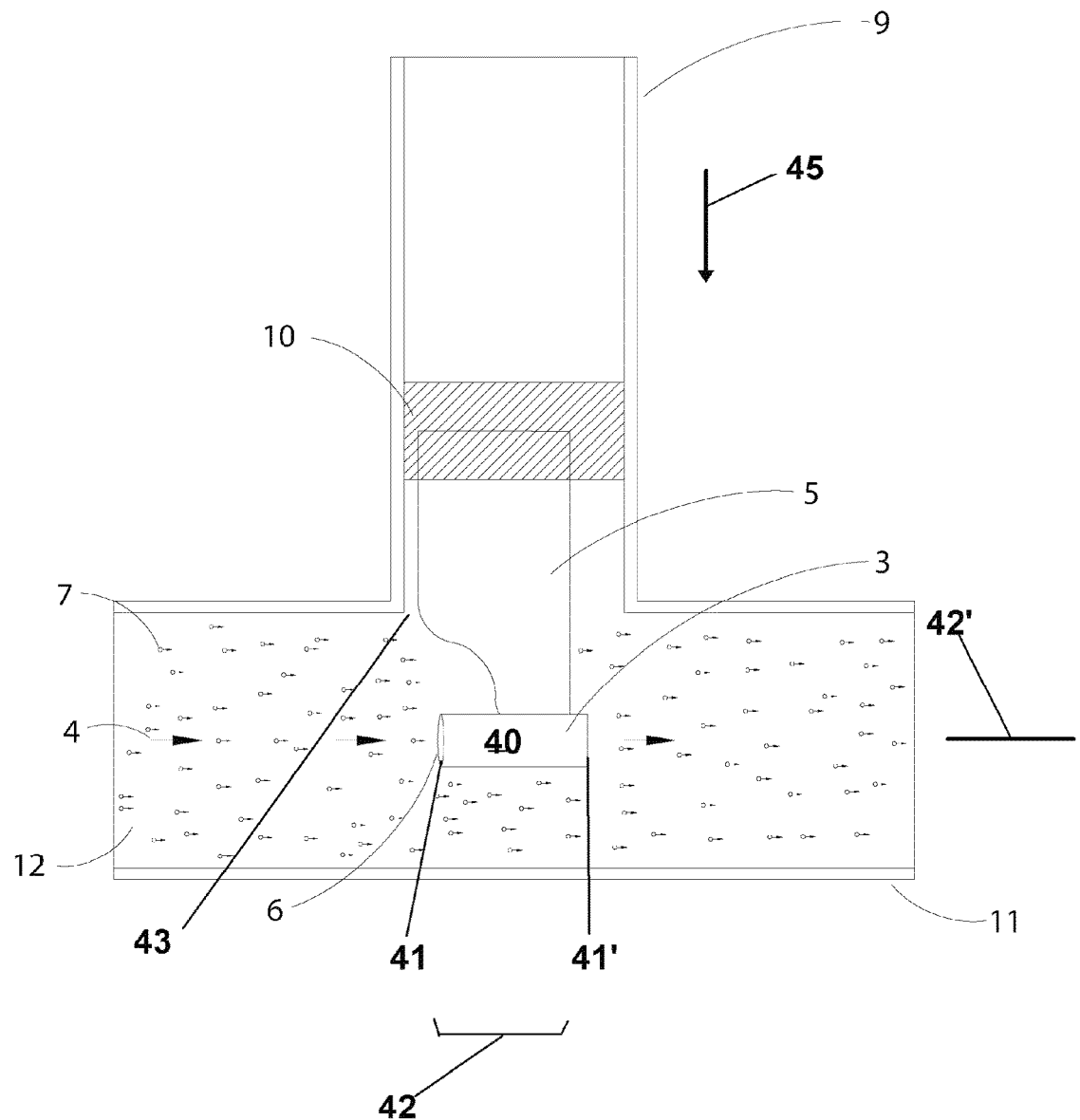
FIG. 2 is a side, partially cut-away view of the invention of FIG. 1, illustrating a sample collection container lowered from a housing into a process gas stream, providing a container having sample gas containing entrained liquid therein.
Figure 3:
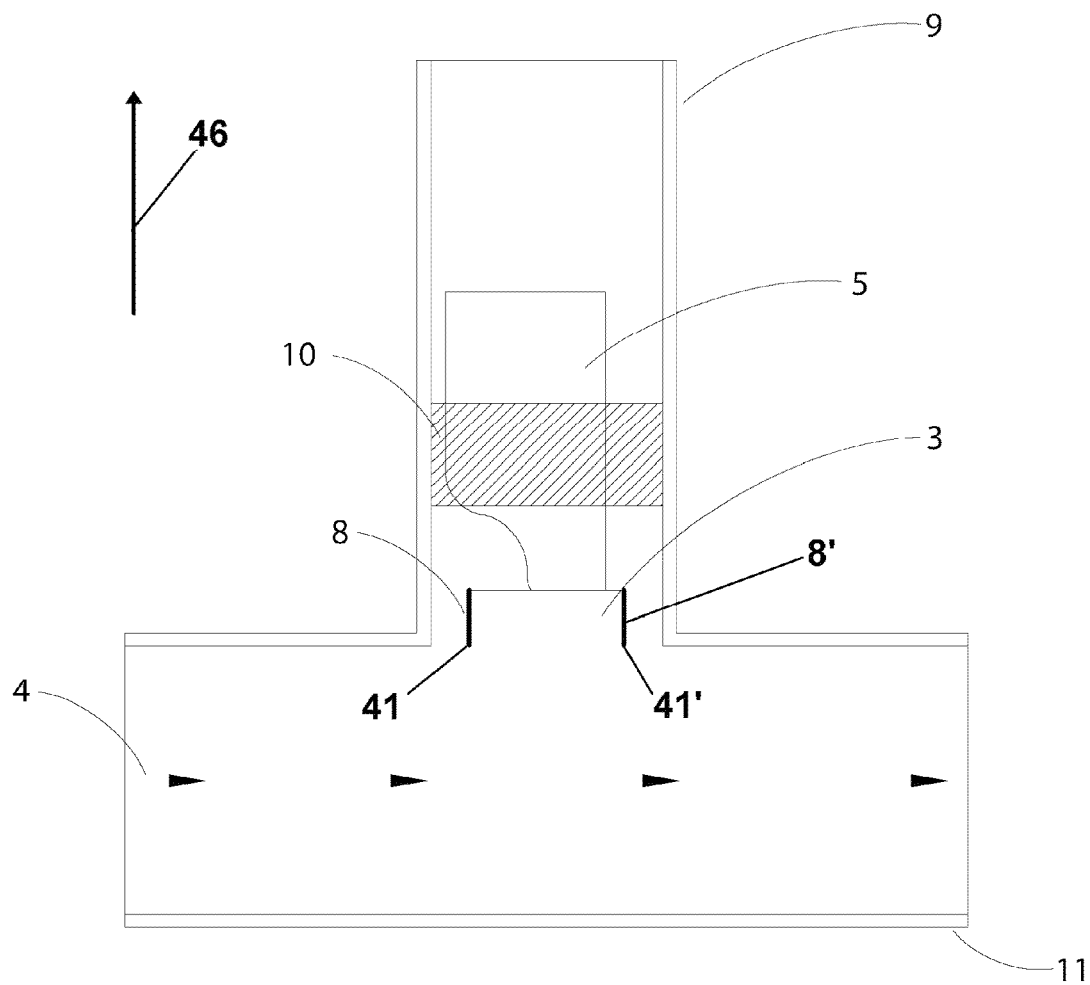

Referencing FIGS. 1-3, a first embodiment of the collection system of the present invention utilizes an open ended container 3, illustrated in the form of a cylinder 40 having first 41 and second 41' ends, a length 42 having a longitudinal or central axis 42', and a passage 44 formed longitudinally therethrough.

The container 3 is mounted to a support/positioning system (further discussed herein) to selectively extend 45 from housing 9 into pipeline 11, positioning the container to allow the unencumbered passage therethrough of a portion of gas or gas/liquid droplet fluid stream 12 with nominal disturbance, said container central axis of said container in alignment with the direction of gas/liquid flow 4. As shown, the housing 9 is mounted to pipeline 11, providing opening 43 into pipeline 11.

The container 3 is constructed of thin wall material, to provide nominal interference with the gas stream, and is suspended by a thin support 5 which is engages the container slightly downstream from its open entry end 6, so as to provide a streamlined attachment surface and overall profile that will minimize the likelihood of appreciable liquid particle flow disturbance.

The collection cylinder or container 3 volume will range from approximately 0.2 cubic inch to 15 cubic inch, depending on sample size required, source fluid pressure, and pipe ID.

Since container 3 is open-ended and in alignment with the flow stream, the gas/liquid flow rate through should be the same as the fluid flowing outside of said container 3. Therefore, the flow can be said to be isokinetic within container 3.

Figure 4:
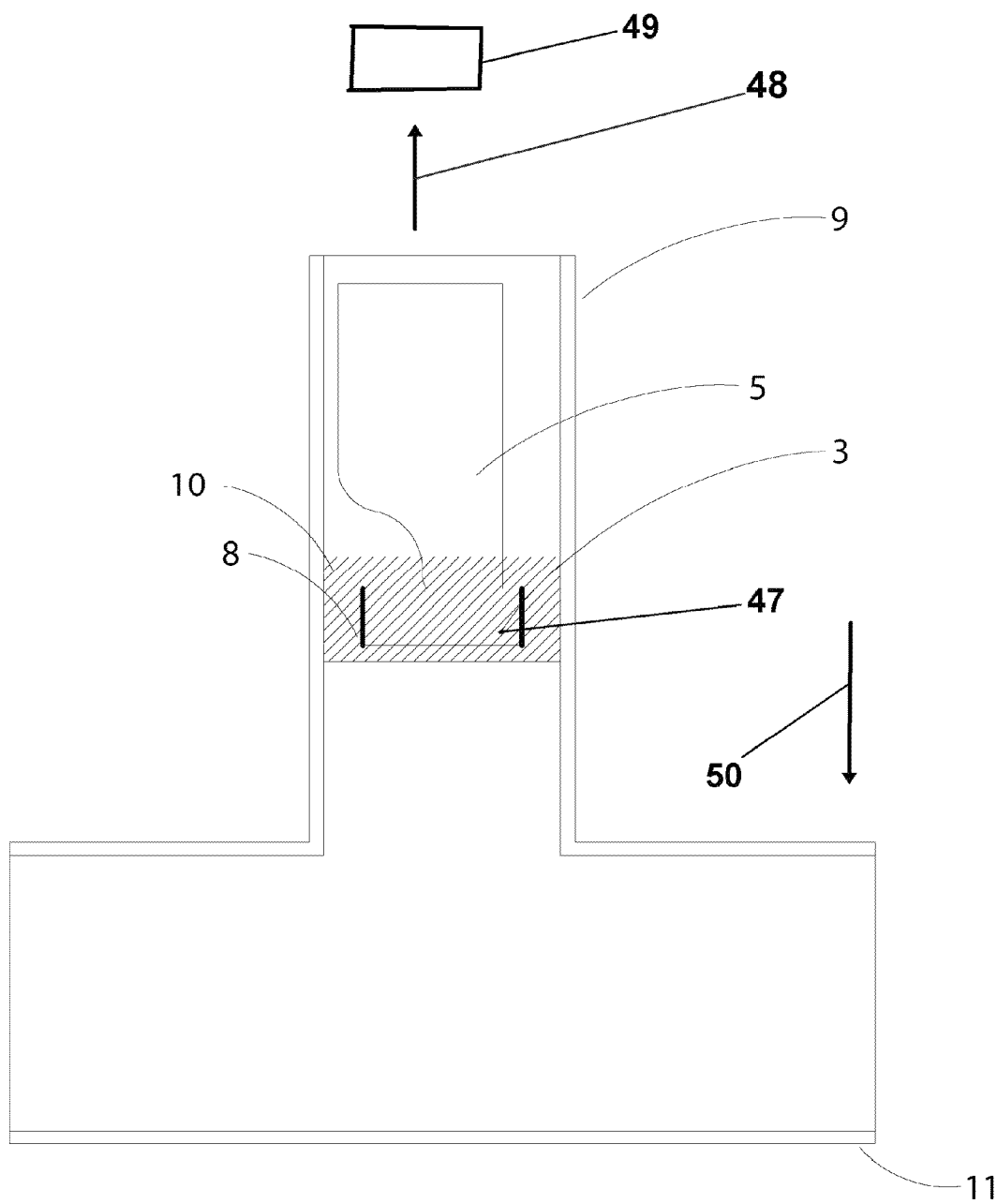
FIG. 4 is a side, partially cut-away view of the Invention of FIG. 1, wherein the sealed container having said sample gas therein is positioned within the housing into a heating zone to heat the container and sample gas contained therein so as to vaporize the liquid entrained in said sample gas, rendering the sample entirely in gas phase.

Referencing FIGS. 3 and 4, a short time after the container 3 is suspended in the gas/liquid flow, it is withdrawn or retracted 46 into housing 9, whereupon the open ends 41, 41' of container 3 are sealed, for example via plugs 8, 8' engaging open ends 41, 41' respectively, providing a sealed container having the gas/liquid droplet sample situated therein.

The sealed container is then heated by a heater (for example, electric resistance or thermoelectric heater, or hydrocarbon fueled heater, or the like) in heating zone 10 in the housing so as to vaporize all entrained liquid in the sealed container, so as to render the sample into a single (gas) phase. The gas is then made to flow 48 via a sample line or the like (not shown) into an external analyzer and/or sample storage container 49 for analysis. Insertion and retraction of container 3 is by external actuation means (not shown) attached to support 5.

To obtain a second sample, the container 3 is unsealed to open its first and second ends (by removing plugs 8, 8', in this example) and container 3 is again extended 50 into the flowing fluid stream 12 to be sampled, where the container thermally interacts with the gas stream to reach temperature equilibrium with same, to "refill" with a fresh sample of gas/liquid droplets before being withdrawn to begin a new cycle.

Referring to FIG. 1, when fully extended into the fluid source, the sampling support 5 can be formed so as to provide a barrier 1 emanating therefrom, positioned so as to close off the opening of the pipe at the housing, so as to minimize fluidic disturbance/turbulence while providing a streamlined fluid flow path through the sample area in the pipeline during sampling.

Referring to FIG. 1, the opening where housing 9 meets the pipeline may be selectively blocked via a barrier 1 having the profile 2 (in the present example, a radial profile) of the pipeline 11, so as to minimize disturbance in the process stream during the sampling operation when the barrier is in place. The barrier 1 may be affixed to the support 5 to raise or lower same as it is raised or lowered, as above, or may be provided in the form of a trap door which is pivotally affixed to the inner walls of the housing, for example.

The present system thereby provides an "static isokinetic" process wherein the container obtains a sample under isokinetic fluid flowing conditions, but the sampled fluid flow ceases as the cylinder is withdrawn from the flowing fluid stream and sealed in the sample container. The static sample is then made into a single phase (gas) by heating under the existing static condition, as discussed above.

This "static isokinetic" sampling process differs from other forms of isokinetic sampling. Conventional "dynamic" isokinetic sampling is designed to insure an isokinetic fluid flow into the opening of a probe and thereon to an external location. The fluid stream velocity (in dynamic systems) must be known and the fluid velocity entering the probe must be controlled, an impractical approach for traditional field sampling of fluids.

In contrast, in the "static isokinetic" sampling process, as a volume of the source fluid flowing through a conduit or pipeline is captured by a container suspended in said source fluid, and as the flow rate during capture remains unchanged, no flow rate measurement or control is required. Said container and trapped source fluid is then withdrawn and isolated in a location outside of the source fluid flowing stream. The fluid is thus isokinetically sampled and withdrawn from the source in a static mode.

The present system insures that container 3 will always be filled isokinetically, even when pipeline velocities are rapidly changing.

This apparatus may also be utilized to advantage even when HC liquids are present. High HC dew point gases are difficult to sample dynamically due to phase changes and resulting composition changes which can be triggered by flow, pressure, and/or temperature.

The sampling cylinder illustrated is round but other geometric shapes would not alter the underlying concept. Accordingly, said "static isokinetic" sampling method may also be executed by other means.

For example, in FIGS. 5, 6, 7, 8a, 8b, 8c, 8d, a support structure 24, comprised of vertical support 19, top plate 13 and bottom plate 16 is extended 51 into the source fluid 26 at an approximate 90 degree angle from the direction of fluid flow.

Figure 5:
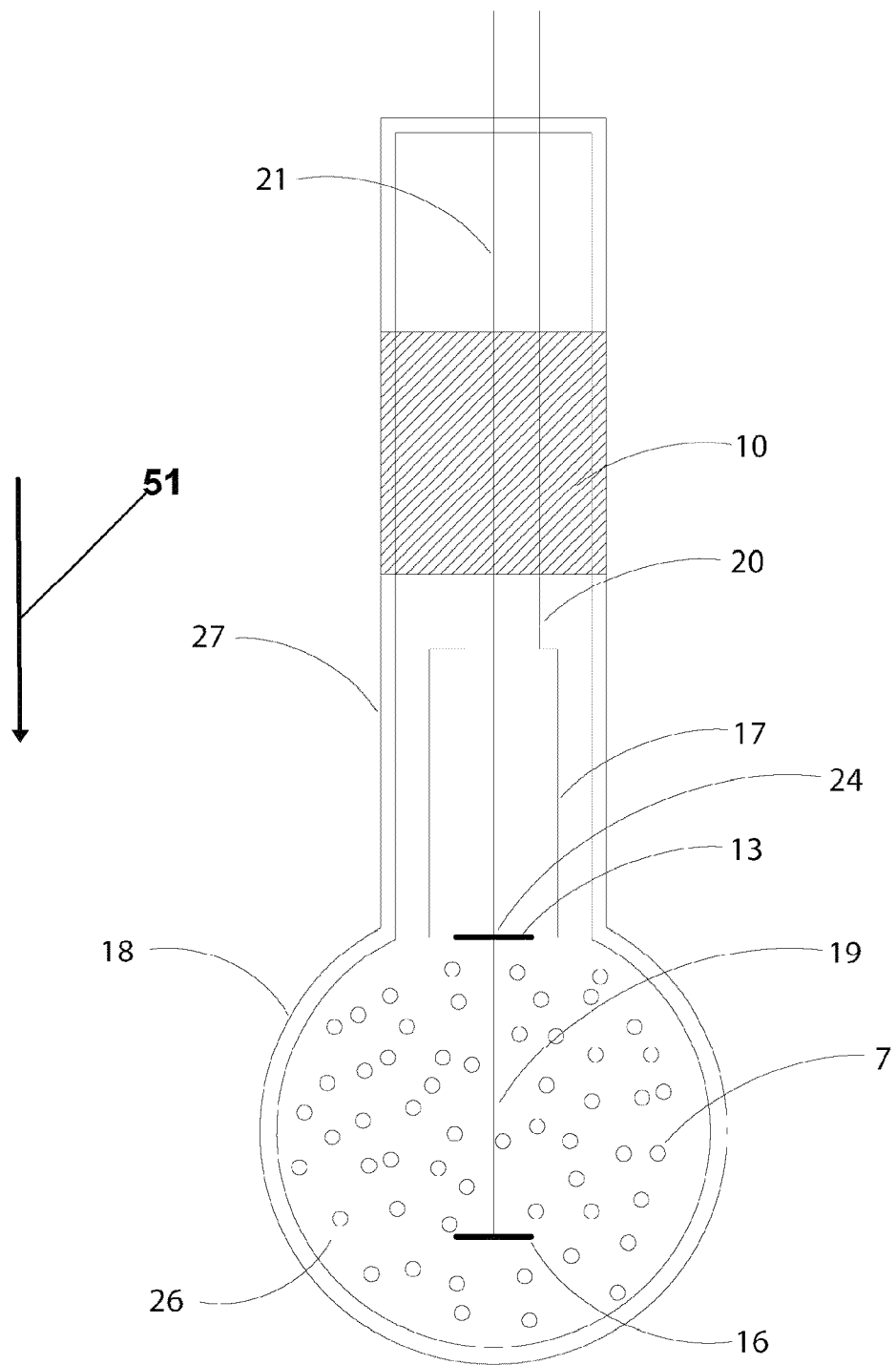
FIG. 5 is an end, partially cut-away view of the second embodiment of the sample collection system of the present invention, illustrating a support structure comprised of vertical support 19, top plate 13 and bottom plate 16 is lowered from a housing into a source fluid 26 in a pipeline at an approximate 90 degree angle from the direction of fluid flow.
Figure 6:
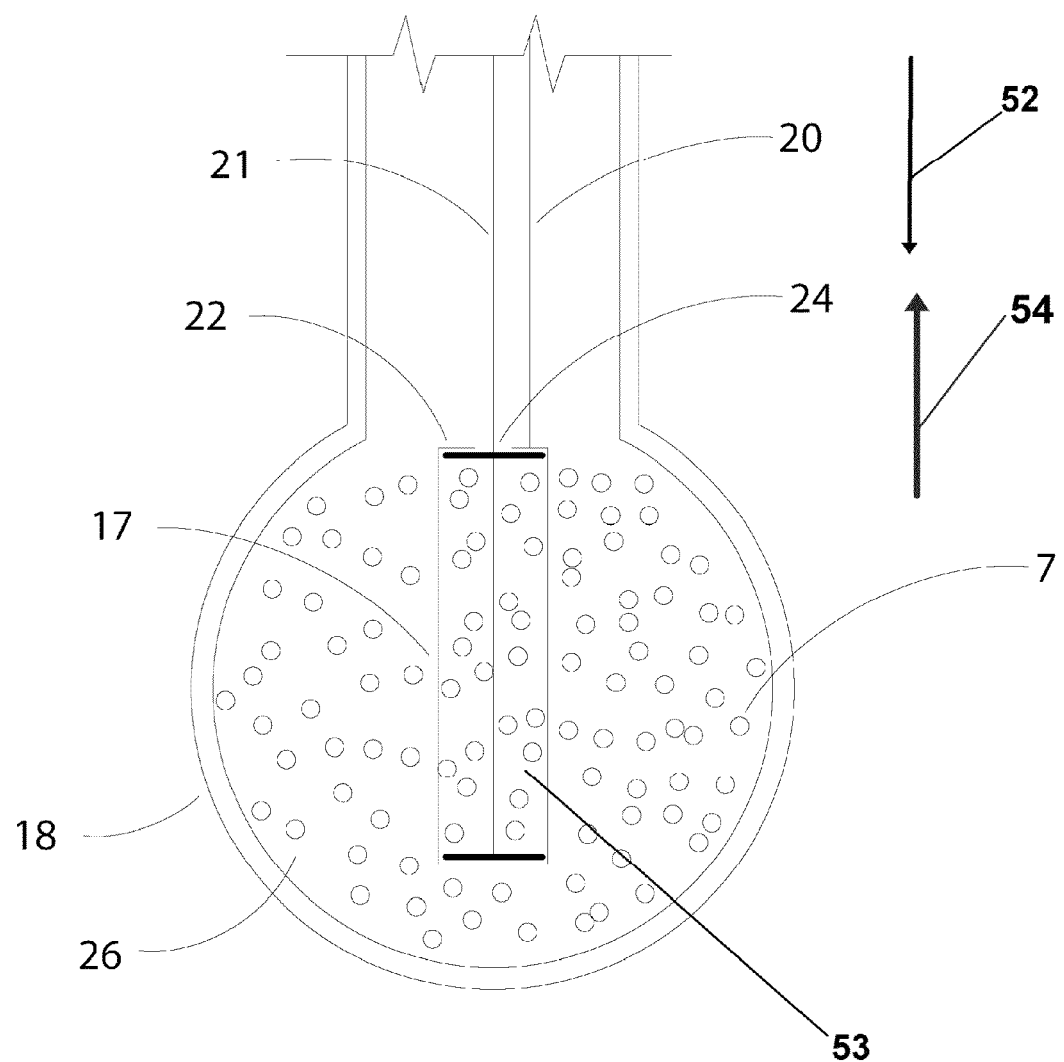
FIG. 6 illustrates a homogenized mixture of small liquid droplets 7 suspended in a gas stream at a collection area where the collection device is positioned, the Figure further illustrating a sample housing which is lowered from the housing to engage top plate 13 and bottom plate 15 to form a sample housing, enclosing a sample of the homogenized gas from the gas stream.
Figure 7:
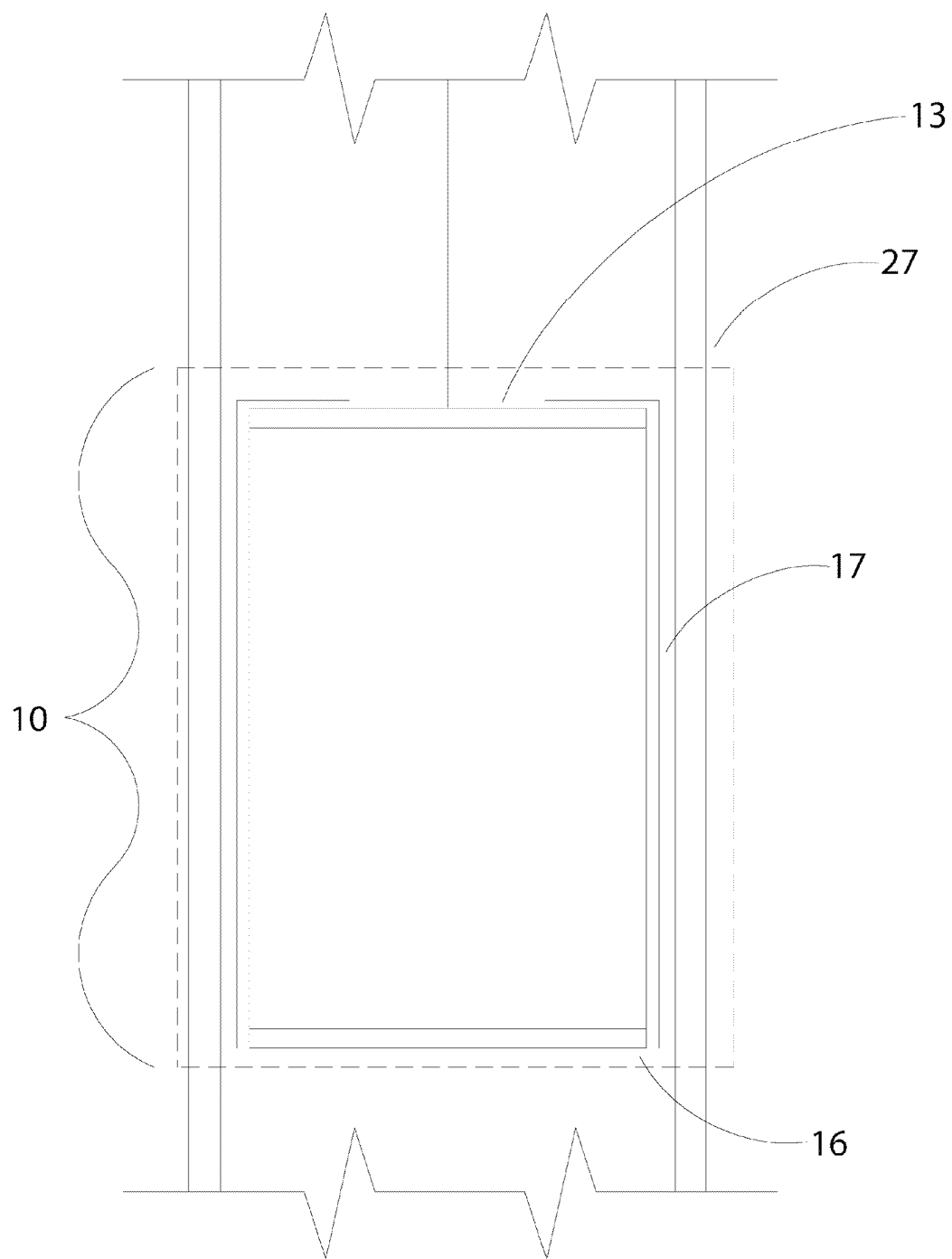
FIG. 7 illustrates a frontal close-up view of the sample housing of FIG. 6.
Figure 8A:
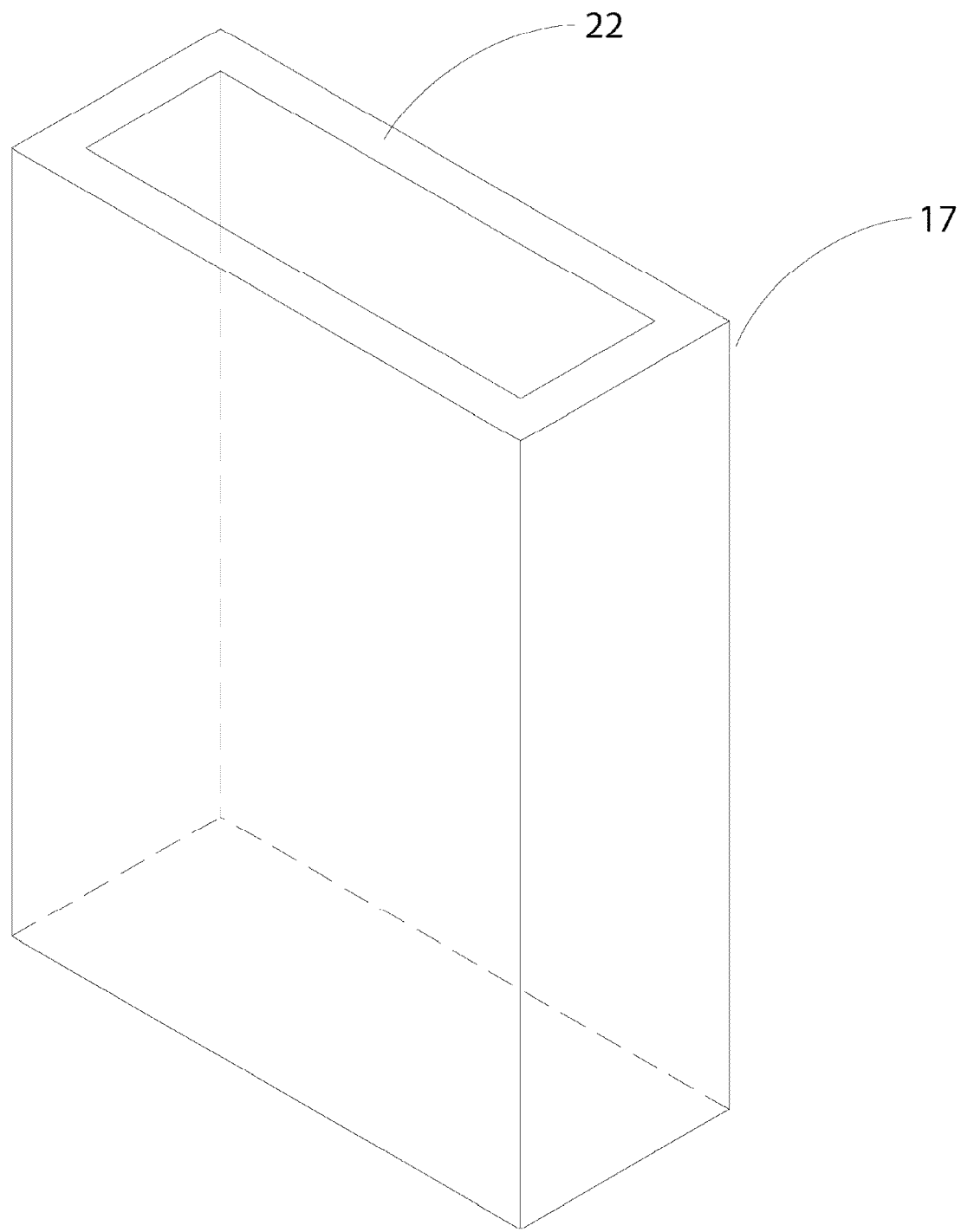
FIG. 8A is an isometric view of the sample housing of FIG. 6.
Figure 8B:
FIG. 8B is an end view of the sample housing of FIG. 6.
Figure 8C:
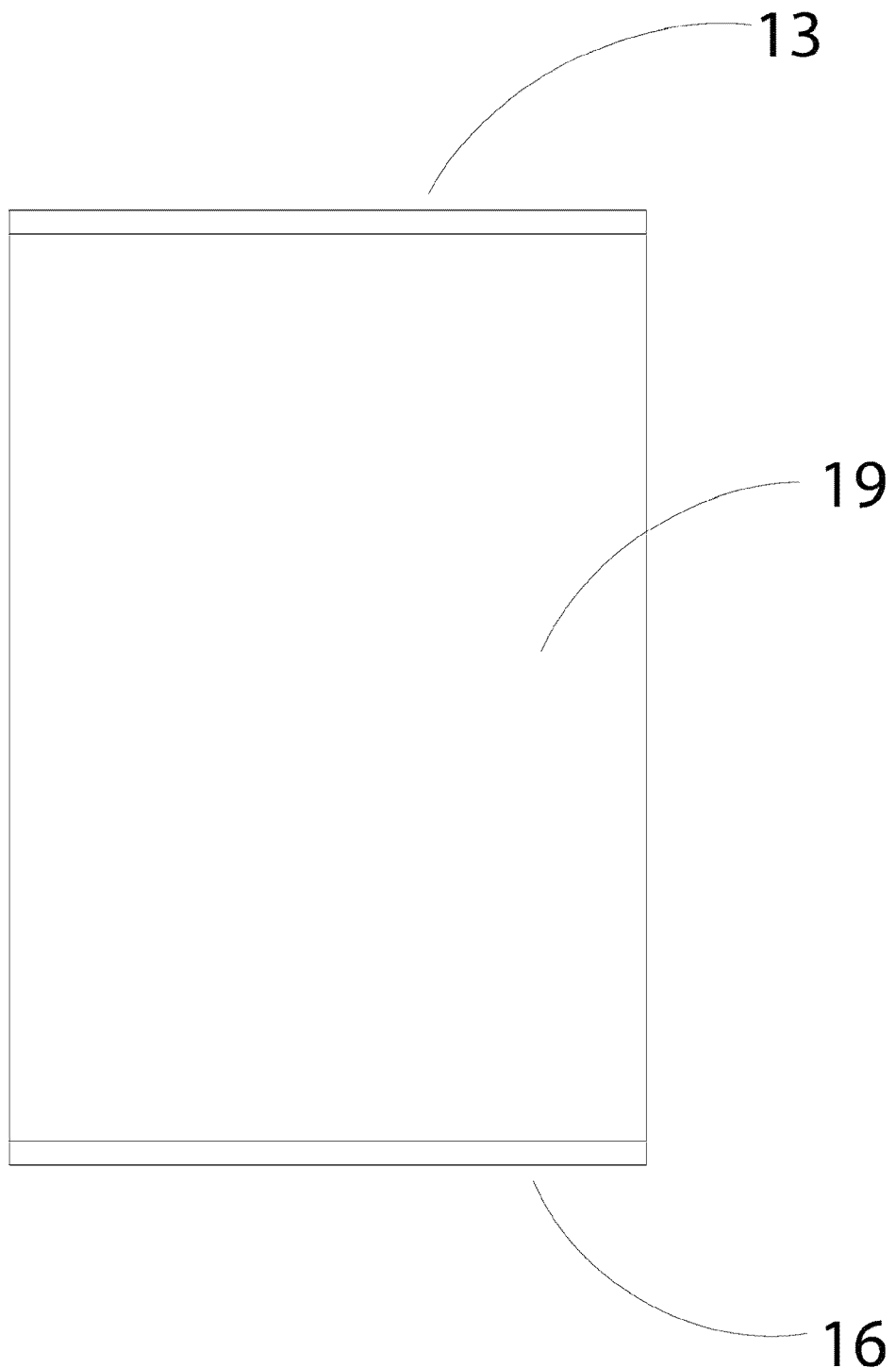
FIG. 8C is a side view of the top plate 13, vertical support 19 and bottom plate 16 of FIG. 5.
Figure 8D:
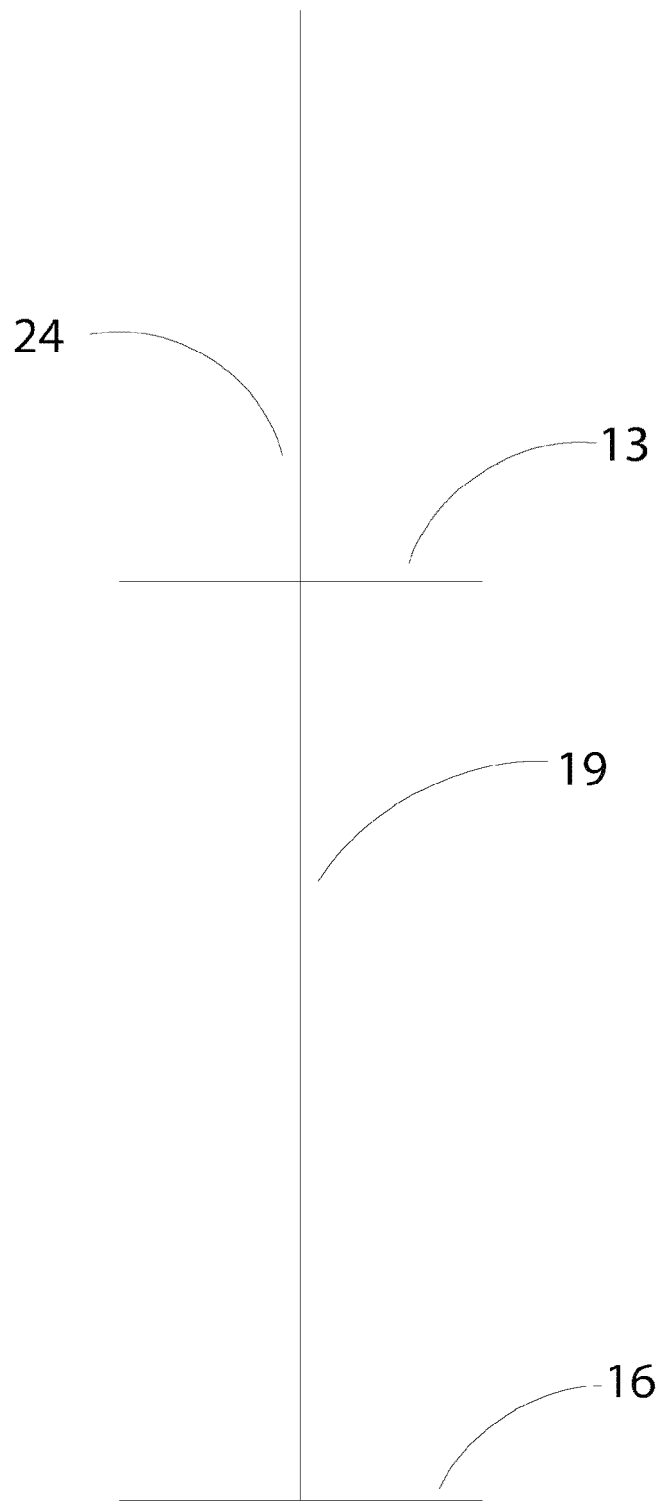
FIG. 8D is an end view of the top plate 13, vertical support 19 and bottom plate 16 of FIG. 8C.

After a brief period sample housing 17, refer to FIGS. 5, 6, and 7, is extended 52 to envelope the area between the first 13 and second 16 plates of support structure 24, with lateral edge 22 engaging the side of first plate 13 distal second plate 16, so as to trap a sample of fluid 26' containing a proportion of liquid droplets 7 therein, providing a contained sample 53. The sample housing 17 and support structure 24 are then retracted 54 into heated zone 10 located in housing 27. The fluids are heated sufficiently to vaporize and homogenize them thoroughly. Said homogenized sample fluid can then be moved to an external location for storage or analysis by a sample conduit, for example.

Retraction and insertion of the actuation members 20, 21 positioning sampling housing 17 and support structure 24 is by external actuation means (not shown).

Figure 9:
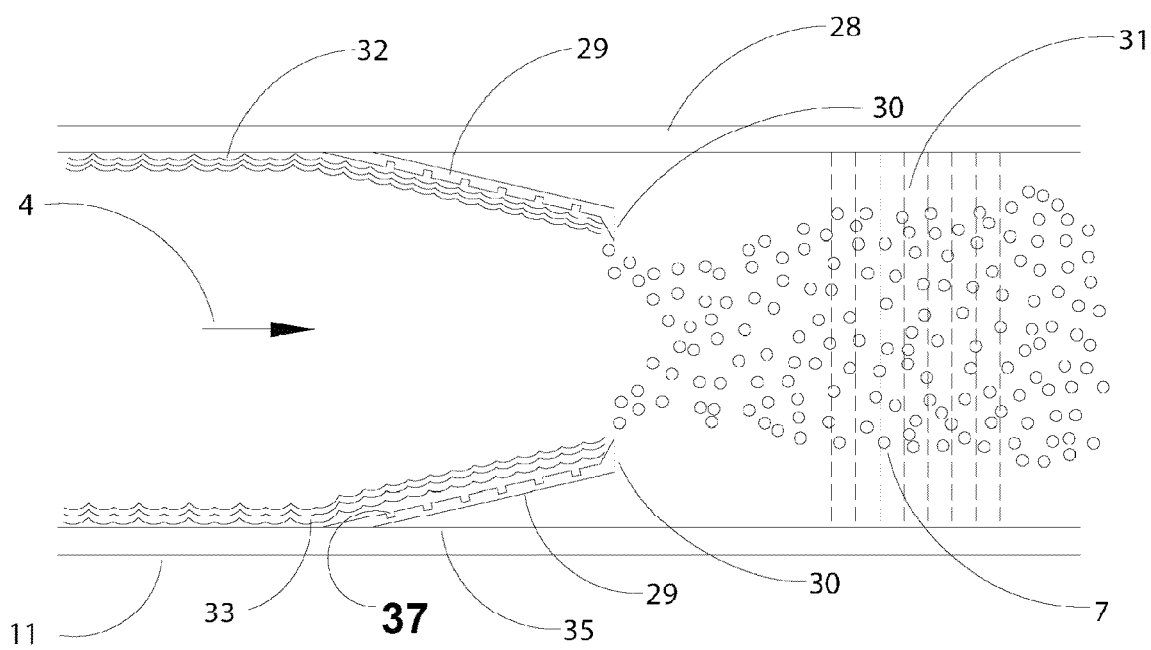
FIG. 9 is a side view of a device to break up entrained liquid in the gas stream for use in the system of the present invention, converting same into small liquid droplets, providing an area suitable as a collection zone wherein there is provided a homogenized gas and liquid droplet fluid stream.

Referring to FIG. 9, where the gas stream contains liquid not in droplet form, such as liquid flowing along the inner wall or at the bottom of the pipeline, the system of the present invention requires that, prior to collection of the sample via the above apparatus, this liquid must be broken into small droplets, in order to provide a collection zone wherein there is provided the desired gas and liquid droplet mixture.

Traditional static mixers are not well suited for this task. The liquid must first be divided into small droplets, suspended into a flowing gas stream and directed away from the inner wall surface of the pipeline. Under those conditions a sample taken across the cross-section of the pipeline will represent both the gas and liquid phases. It is important that liquid is not flowing along the inner pipe wall or at the bottom of the pipeline in the sample area.

Where the gas stream to be sampled requires conditioning to break up the entrained liquid into small droplets, the present invention provides a conditioning apparatus which is provided upstream of the collection area, situated in line with the gas stream to receive the gas stream, and having a downstream exit having a sloped constriction 29 and 29 (Refer to FIG. 9) wherein the fluid flows in direction 4, said constriction 29 terminating with a sharp lip 30 and 30 to break up entrained liquids 32 and 33 into droplets 7 by the force and turbulence of the flowing gas. In the present example, the lip is at a 90° angle relative to the fluid flow and will range from 0.05" to 0.5" in height.

Said lip 30 may be geometrically shaped or having a surface composition (via coating for example) to enhance droplet 7 formation. Sloped constriction of conduit wall 35 of the conditioning apparatus will force liquid 32 and 33 away from the inner pipe wall 35 downstream from said lip 30. The constriction member slope relative to the inner pipe wall will range from 5° to 45°.

By breaking up the entrained fluid into suspended droplets to homogenize same into the gas stream, even if within a limited sampling zone 31, one is able to obtain a sample within that sampling zone 31 containing the correct proportion of liquid.

In comparing the constriction to "orfice plate" flow measurement the maximum constriction ID would be D2 and the pipe ID would be D1. The fractional constriction referenced above is equal to the Beta ratio of an orfice plate which is equal to D2/D1. Using orfice plate analogy the sample collection zone would probably be in the vena contracta zone.

Droplets which are already suspended in the flowing gas before entering sloped constriction 29 and 29' flow into the sampling zone 31 without alteration. Sampling is preformed in sampling zone 31 at an optimum distance downstream of the droplet formation area. Other techniques may be utilized to achieve droplet formation of entrained liquid.

An example is utilizing a plurality of Helmholtz resonator cavities 37 formed in an inner surface in contact with the flowing gas to create sonic energy sufficient to promote droplet formation. Said sonic energy of ultrasonic frequency is a well known method for breaking up a flowing liquid into small droplets. Other types of cavities and methods for producing sonic energy by using the flowing fluid may also be employed in that manner. An external source for vibrating the inner pipe wall, not shown, may also be utilized to aid in droplet formation.

Helmholtz Cavity Dimensions

The following formula will be utilized to produce ultrasonic energy in the range of 20 KHz to 100 KHz.

$$fr = \frac{c}{2\pi}\sqrt{\frac{\pi r^2}{l'_{eff}}}$$

Where:
fr=resonance frequency of each cavity
c=speed of sound
r=radius of the cavity neck
leff=effective length of the neck
v=volume of the cavity Helmholtz cavities have a neck and a cavity which may be constructed by overlaying perforated plates in which the holes in a first plate comprises the cavity neck and the holes in a second place comprise the cavity volume. When two such plates are in alignment and placed over a third plate which is unperforated, a plurality of Helmholtz cavities are created.

A combination of methods may be utilized for breaking up entrained liquid into small droplets. Droplet size requirement will depend upon the gas velocity. Gas velocity should be sufficient to maintain suspension of the liquid droplets beyond the static isokinetic sampling point.

Accordingly, prior to specimen collection, the entrained liquid is first broken into small droplets 7 then homogenized into the gas stream 12 (as discussed above).

Exemplary Specification Ranges
ID of pipe 2" to 30"
Pressure 30 PSIG to 5,000 PSIG
Temperature 50° F. to 120° F.
Flow rate 10,000 cubic feet per day to 1 billion cubic feet per day
Velocity of gas 10 feet per second to 100 feet per second
Ratio of gas to entrained liquid range 99:1 to 99.9:1
Constriction member 0.5 to 0.99 constriction of pipe ID Vertical supports are constructed of steel, typically stainless steel and range in thickness from 0.02: to 0.10".

The leading edge of the cylinder, upper and lower plates, and supports may be sharpened so as to minimize fluid flow disturbances.

LISTING OF ELEMENTS

1 barrier
2 radial profile
3 container
4 direction of flow
5 support
6 open entry end
7 small droplets
8 plugs
9 housing
10 heating zone
11 pipeline
12 fluid stream
13 top plate
14 lowered
15
16 bottom plate
17 sample housing
18 pipe wall
19 vertical support
20 actuation member
21 actuation member
22 lateral edge
24 support structure
26 source fluid, 'fluid sample (added' verify)
27 housing
28 pipeline
29, 29' sloped constriction
30, 30' sharp lip
31 sampling zone
32 entrained liquid
33 entrained liquid
34
35 pipe wall
36 droplets
37 helmholtz resonator cavities
40 cylinder
41 first end
41' second ends
42 length
42' central axis
43 opening
44 passage
45 external
46 retract
47 gas
48 flow
49 container
50 extended
51 extended
52 extended
53 contained sample
54 retracted The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

What I claim is:

1. The method of sampling a gas stream having entrained liquid therein in a pipeline, comprising the steps of:
    ai. Providing a sample container having a length having first and second ends forming a passage therebetween, said length of said sample container formed to selectively fit within said pipeline;
    aii. Providing a support engaging said sample container, said support formed to selectively direct said sample container into and out of said pipeline;
    aiii. said sample container and support having a streamlined profile;
    b. positioning said support so as to position said sample container into said gas stream such that said length of said sample container is aligned with said gas stream so as to minimize flow disturbance;
    c. allowing said gas stream to pass into said first end of said sample container, through said passage, and out of said second end, providing isokinetic flow through said sample container, while providing sample fluid contents there between;

d. blocking said first and second ends of said sample container so as to contain said sample fluid contents within the passage of said sample container, providing an enclosed sample container containing a sample.

2. The method of claim 1, wherein there is further provided the added step "e" of heating said enclosed sample container to vaporize the sample fluid contents therein, providing a vaporized sample.

3. The method of claim 2, wherein there is further provided the added step "f" of analyzing said vaporized sample.

4. The method of claim 1, wherein said gas stream has a velocity, and wherein there is provided after step aiii the added step a1 of dispersing entrained liquid in said pipeline into liquid droplets, while utilizing the velocity of said gas stream to suspend said droplets in said gas stream, so as to form a sample zone downstream therefrom.

5. The method of claim 4, wherein in step a1 said entrained liquid is dispersed into liquid droplets suspended by said gas stream by flowing said entrained liquid across a sloped constriction terminating with a sharp lip formed to break up entrained liquids into droplets by the force and turbulence of said gas stream flowing therethrough.

6. The method of claim 5, wherein in step b said sample container is positioned in said sample zone.

7. The method of sampling a gas stream having entrained liquid therein in a pipeline, comprising the steps of:
   ai. providing a housing having a length and a width, and an opening formed through the wall of said pipeline, so as to provide access to said gas stream having liquid entrained therein;
   aii. providing a sample container having a length having first and second open ends, said length of said sample container formed to selectively fit within said housing;
   aiii. providing a support engaging said sample container, said support formed to selectively direct said sample container from said housing to said pipeline and visa versa;
   aiv. said sample container and support having a streamlined profile;
   b. positioning said support so as to position said sample gas container from said housing into said gas stream such that said length of said sample container is aligned with said gas stream so as to minimize flow disturbance;
   c. allowing said gas stream to pass into said first end of said sample container and out of said second end, providing isokinetic flow through said sample container, while providing sample fluid contents there between;
   d. positioning said support so as to move said sample gas container from said gas stream into said housing, while maintaining said sample fluid contents in said sample container;
   e. blocking said first and second open ends of said sample container so as to contain said sample fluid contents within said sample container, providing an enclosed sample container within said housing.

8. The method of claim 7, wherein there is further provided the added step "f" of heating said enclosed sample container to vaporize the sample fluid contents therein, providing a vaporized sample.

9. The method of claim 8, wherein there is further provided the added step "g" of analyzing said vaporized sample.

10. The method of claim 9, wherein there is further provided after step b the added step "b1" of blocking the opening of said housing at said pipeline with a barrier having the profile of the inner diameter of the pipeline, so as to streamline the area for the sampling operation.

11. The method of claim 10, wherein said barrier is affixed to said support.

12. The method of claim 10, wherein said barrier is pivotally affixed to the housing at the opening of the pipeline to form a trap door to selectively open to allow the passage of said sample container there through.

13. The method of claim 7, wherein said gas stream has a velocity, and wherein there is provided after step aiv the added step a1 of dispersing entrained liquid in said pipeline into liquid droplets, while utilizing the velocity of said gas stream to suspend said droplets in said gas stream, so as to form a sample zone downstream therefrom.

14. The method of claim 13, wherein in step a1 said entrained liquid is dispersed into liquid droplets suspended by said gas stream by flowing said entrained liquid across a sloped constriction terminating with a sharp lip formed to break up entrained liquids into droplets by the force and turbulence of said gas stream flowing therethrough.

15. The method of claim 14, wherein in step b said sample container is positioned in said sample zone.

16. The method of claim 13, wherein in step a1 said entrained liquid is dispersed into liquid droplets by utilizing a plurality of Helmholtz resonator cavities formed in an inner surface in contact with the flowing gas to create sonic energy such that liquid flowing thereover would disperse into droplets suspended by said gas stream.

17. An apparatus for sampling a gas stream having entrained liquid therein in a pipeline, comprising:
   a housing having a length and a width, and an opening formed through the wall of said pipeline, so as to provide access to said gas stream having liquid entrained therein;
   a sample container having a length having first and second open ends, said length of said sample container formed to selectively fit within said housing;
   a support engaging said sample container, said support formed to selectively direct said sample container from said housing to said pipeline such that said length of said sample container is aligned with said gas stream so as to minimize flow disturbance, as well as repositioning said sample container from said pipeline into said housing;
   said sample container and support having a streamlined profile;
   first and second plugs associated with said housing, said first and second plugs formed to selectively engage said first and second open ends of said sample container, respectively, upon said sample container being positioned from said pipeline into said housing, so as provide an enclosed sample container;
   a heater associated with said housing to selectively heat said enclosed sample container.

18. The apparatus of claim 17, wherein said support has associated therewith a barrier having the profile of the inner diameter of the pipeline, said barrier situated on said support such that, upon positioning said sample container within said pipeline for sampling, said barrier blocks the opening of said housing at said pipeline, so as to provide a streamlined flow thereby.

19. The apparatus of claim 17, wherein a barrier having the profile of the inner diameter of said pipeline is pivotally affixed to the housing at the opening of the pipeline, to form a trap door to close said opening, while selectively pivoting to allow the passage of said sample container there through.

20. The apparatus of claim 17, wherein upstream said gas stream from said sample container there is provided an apparatus for dispersing entrained liquid into liquid droplets suspended by said gas stream, so as to form a sample zone at said sample container, comprising:

a slope having a first end engaging said inner wall of said pipeline terminating in a constriction downstream said first end, said constriction having and end having a sharp lip formed to utilize the force of said gas flowing therethrough to urge said entrained liquid traversing said slope to break up into droplets by the force and turbulence of said gas stream flowing therethrough such that said droplets are suspended by said gas stream through said sample zone.

21. The apparatus of claim 17, wherein upstream said gas stream from said sample container there is provided an apparatus for dispersing entrained liquid into liquid droplets suspended by said gas stream, so as to form a sample zone at said sample container, comprising:

a slope having an end engaging said inner wall of said pipeline, said slope having a plurality of Helmholtz resonator cavities formed thereon in contact with said gas stream so as to facilitate the creation of sonic energy such that liquid flowing thereover would disperse into droplets suspended by said gas stream.

* * * * *